United States Patent [19]

Bokerman et al.

[11] Patent Number: 5,051,247

[45] Date of Patent: Sep. 24, 1991

[54] SILANE PRODUCTS FROM REACTION OF SILICON MONOXIDE WITH ORGANIC HALIDES

[75] Inventors: Gary N. Bokerman; John P. Cannady, both of Madison, Ind.; Charles S. Kuivila, LaGrange, Ky.

[73] Assignee: Dow Corning Corporation, Midland, Mich.

[21] Appl. No.: 576,908

[22] Filed: Sep. 4, 1990

[51] Int. Cl.$^5$ .................. C01B 33/107; C07F 7/16
[52] U.S. Cl. ...................... 423/342; 252/182.3; 423/347; 556/472
[58] Field of Search ............... 423/342, 347; 556/472, 556/474, 476; 252/182.3

[56] References Cited

U.S. PATENT DOCUMENTS

| | | | |
|---|---|---|---|
| 3,660,448 | 5/1972 | Schaschel | 556/410 |
| 3,660,449 | 5/1972 | Schaschel | 556/430 |
| 3,660,450 | 5/1972 | Timms | 556/434 |
| 3,660,451 | 5/1972 | Schaschel | 556/452 |
| 3,661,961 | 5/1972 | Schaschel | 556/451 |
| 4,585,646 | 4/1986 | Gomberg | 423/658.2 |

*Primary Examiner*—Olik Chaudhuri
*Assistant Examiner*—Ken Horton
*Attorney, Agent, or Firm*—William F. Boley

[57] ABSTRACT

The present invention is a process for preparing silanes from the reaction of solid silicon monoxide with organic halides. The solid silicon monoxide is reacted with the organic halide in the presence of a catalyst which can increase the conversion of silicon monoxide to silanes and partially select for the type of silanes produced. The process may employ an activation step in which the solid silicon monoxide is activated by heating in an inert atmosphere. Activation of the silicon monoxide can increase silicon conversion and alter the type of silanes produced.

27 Claims, No Drawings

SILANE PRODUCTS FROM REACTION OF SILICON MONOXIDE WITH ORGANIC HALIDES

BACKGROUND OF INVENTION

The present invention is a process for preparing silanes by the reaction of silicon monoxide with organic halides, in the presence of a catalyst. The described catalysts increase conversion of the silicon monoxide and alter the selectivity of the described processes for silane products. Selectivity for product silanes can be furthered altered by an activation step comprising the heating of the silicon monoxide in an inert atmosphere.

Silanes are primarily produced by the direct reacting of silicon with organic halides or hydrogen halides, as first disclosed by Rochow and his co-workers in the 1940's. A significant portion of the cost of this process is the cost of the silicon metal used as a feed material. Silicon metal is typically produced in an electric-arc furnace by the carbothermic reduction of silicon dioxide. This process requires high temperature and high energy consumption, which is reflected in the cost of silicon metal.

Silicon monoxide can be produced at a lower temperature than silicon and, thus, may serve as a less expensive raw material for the production of silanes. The instant invention describes a process whereby potentially less expensive solid silicon monoxide can be reacted with alkyl halides to produce silanes.

Schaschel, in a series of patents, described a process for preparing organosilicon polymers by reacting silicon monoxide with organic compounds. The methods of the described invention involved preparation of silicon monoxide vapors from solid silicon monoxide by heating the same under vacuum to about 1200° C. to 1300° C.; mixing in a chamber having cooled walls the gaseous silicon monoxide formed thereby, with an excess of a volatile organic compound to form a mixture; and condensing the mixture to obtain the organosilicon polymer. The reaction is reported to occur on the cold surface of the chamber to form the polymer thereon.

The reactions of organic compounds taught by Schaschel are: Schaschel, U.S. Pat. No. 3,660,448, issued May 2, 1972, organic compounds containing active hydrogen atoms such as alcohols and amines; Schaschel, U.S. Pat. No. 3,660,449, issued May 2, 1972, organic compounds containing a triple bond such as acetylene; Schaschel, U.S. Pat. No. 3,660,451, issued May 2, 1972, organic monohalides such as 1-bromobutane; and Schaschel, U.S. Pat. No. 3,661,961, issued May 9, 1972, aliphatic hydrocarbons such as n-octane.

Timms, U.S. Pat. No. 3,660,450, issued May 2, 1972, teaches a process for reacting gaseous silicon monoxide with an aromatic compound containing at least one benzene nucleus, the compound having no triple bonds and having no active hydrogen atoms. The described process is similar to that previously described for the Schaschel series of patents.

Gomberg, U.S. Pat. No. 4,585,646, issued April 29, 1986, teaches a process where $Si_2OCl_6$ is irradiated to form solid SiO. The solid SiO is isolated and reacted at 500° C. with HCl. The process is reported to form tetrachlorosilane, water, and hydrogen gas. No SiH products were produced. In addition, no activation process for the silicon monoxide or use of a catalyst is taught.

SUMMARY OF INVENTION

The described invention is a process for preparing silanes from the reaction of solid silicon monoxide with organic halides. The solid silicon monoxide is reacted with the organic halide in the presence of a catalyst which can increase the conversion of silicon monoxide to silanes and partially select for the type of silanes produced. The process may employ an activation step in which the solid silicon monoxide is activated by heating in an inert atmosphere. Activation of the silicon monoxide can increase silicon conversion and alter the type of silanes produced.

DESCRIPTION OF INVENTION

A process for producing silanes by the reaction of silicon monoxide with organic halides is described. The process comprises:

(A) contacting silicon monoxide, an organic halide of formula $$RX,$$

where X is a halogen and R is selected from a group consisting of alkyl and alkenyl radicals of one to six carbon atoms, and a catalyst effective in facilitating reaction of the solid silicon monoxide with the organic halide; at a temperature of 200° C. to 1200° C.; and (B) forming silanes of formula $$H_aR_bSiX_{4-a-b},$$

where a is an integer from 0 to 4, b is an integer from 0 to 4, a+b is an integer from 0 to 4, and R and X are as previously described.

The contacting of the solid silicon monoxide, organic halide, and catalyst can be effected in any standard reactor for effecting contact of gases with particulate solids. The process can be conducted, for example, in a fixed-bed reactor, a stirred-bed reactor, a vibrating-bed reactor, or a fluidized-bed reactor.

The source of the silicon monoxide is not critical to the instant described process. However, a preferred source is silicon monoxide produced by the carbothermic reduction of silicon dioxide, since this source allows for potential energy savings incurred by not requiring the total reduction of silicon dioxide to silicon.

The solid silicon monoxide can be in any convenient particulate form, for example, chips, flakes, powder, or granules. A range of useful particle sizes is about 0.5 micron to 120 mesh. A preferred particle size range is about two micron to about 320 mesh. The term "about," is meant to include similar particle sizes which give comparable levels of silicon monoxide conversion and similar product selectivity.

In general, the smaller the particle size of the silicon monoxide, the higher the conversion of silicon monoxide to silanes. The lower end of the particle size range is limited primarily by the ability to efficiently make and handle the particulate silicon monoxide. Silicon monoxide of particle size greater than that described will work in the instant process, however, conversion of silicon monoxide to silanes may be reduced.

The solid silicon monoxide is contacted with an organic halide of formula RX, where X is a halogen and R is selected from a group consisting of alkyl and alkenyl radicals of one to six carbon atoms. The carbon atoms of R can be in a straight or branched-chain arrangement.

The alkyl radical can be, for example, methyl, ethyl, propyl, butyl, pentyl, hexyl, isopropyl, isobutyl, or tert-butyl. The preferred alkyl radical is methyl or ethyl. The alkenyl radical can be, for example, vinyl, allyl, butenyl or hexenyl. The preferred alkenyl radical is vinyl. The halogen, X, can be a bromide, chloride, fluoride, or iodide atom. The preferred halide is chloride.

The solid silicon monoxide and organic halide are contacted in the presence of a catalyst effective in facilitating reaction of the solid silicon monoxide with the organic halide. By effective, it is meant chemical elements and compounds thereof which, in the presence of an organic halide, increase the of conversion of silicon monoxide to silanes, increase the rate of conversion, or modify the distribution of silane products. Any or all of the aforementioned effects may be an indication of effectiveness of the catalyst.

Materials which are effective catalysts in the described processes are metal and metal compounds selected from the group consisting of: copper and copper compounds, tin and tin compounds, zinc and zinc compounds, antimony and antimony compounds, mercury and mercury compounds, iron and inorganic iron compounds, manganese and manganese compounds, nickel and nickel compounds, phosphorous, metal phosphides, metal phosphorous alloys, aluminum and aluminum compounds, and mixtures thereof.

A preferred catalyst is cuprous chloride (CuCl) alone or in combination with aluminum and $AlCl_3$. A more preferred catalyst is a mixture consisting of CuCl in combination with tin, brass, aluminum, and a copper and phosphorous alloy. Even more preferred, is when the catalyst is a mixture which results in the following final concentrations of metal and metal compounds in a silicon monoxide and catalyst composition: 3.0 to 20 weight percent CuCl, 10 to 200 ppm tin, 300 to 1900 ppm brass, 760 to 4600 ppm aluminum, and 1000 to 6100 ppm of a copper and phosphorous alloy.

A useful concentration of catalyst is considered to be one to 20 weight percent of the combined catalyst and silicon monoxide weight. Lower levels of catalyst may be used, but conversion of silicon monoxide will be reduced. Higher levels of catalyst may be used, which result in increased conversion of silicon monoxide, however, selectivity for greater alkylated silanes tends to decrease at these higher levels.

A preferred catalyst concentration is where the catalyst is present at three to 18 weight percent of the combined catalyst and silicon monoxide weight.

The catalyst can be in any convenient particulate form, such as powder, granule, flake or chip. The mixture can be formed by standard means for mixing particulate materials. For best results, it is preferred that the catalyst be distributed uniformly throughout the particulate silicon monoxide.

Increased conversion of silicon monoxide to silanes, as well as shifts in selectivity for products formed, can be effected by heat activation of the silicon monoxide. The silicon monoxide and catalyst can be combined prior to the activation step, or, the silicon monoxide can be activated first and subsequently combined with the catalyst. The silicon monoxide may be activated during its manufacture. The preferred activation procedure is to combine the silicon monoxide and catalyst prior to the activation step.

The solid silicon monoxide, in particulate form, may be activated by heating at an activation temperature of 50° C. to 1200° C. in an inert atmosphere. A preferred activation temperature range is about 200° C. to about 1050° C. By "about," it is meant any similar temperature which gives comparable silicon monoxide conversion and product selectivity under similar process conditions. In general, an activation time of 0.5 to 20 hours has been found to be useful, when the activation temperature range is 50° C. to 1200° C. Preferred is an activation time of one to 20 hours, when the activation temperature range is 200° C. to 1200° C.

The silicon monoxide is activated in an environment which has been purged of oxygen. Typically, the silicon monoxide will be activated in the reactor in which it is to be contacted with the organic halide. The reactor can be purged of oxygen, for example, by means of a vacuum or an inert purging gas. The purging gas can be any gas which is inert to the silicon monoxide particles or contaminates thereof. Examples of purging gases are argon, helium, krypton, neon, and nitrogen. Helium and nitrogen are preferred gases for purging.

The silicon monoxide, non-activated or activated, is contacted with catalyst and an organic halide at a temperature of 200° C. to 1200° C. to form product silanes. A preferred reaction temperature is about 300° C. to about 900° C. By "about," it is meant similar temperatures which give comparable results under comparable process conditions.

Preferred conditions are where an organic halide gas is passed through a reactor bed of particulate silicon monoxide, mixed with catalyst, at a rate sufficient to allow product silanes to form. The optimal reaction time for an organic halide with silicon monoxide will be dependent upon activation conditions for the silicon monoxide, type of catalyst, reaction temperature, concentration of alkyl halide, and desired conversion of silicon monoxide. In general, reaction times between about four and 50 hours have been found useful. Shorter reaction times may be employed, but with reduced conversion of silicon monoxide. Longer reactions times may also be employed to advantage, depending upon the continuing presence of silicon monoxide in the reactor.

The product silanes as well as excess organic halide is collected by standard means, for example, a cold trap. If desired, the excess organic halide can be isolated and recycled to the process. The product silanes may be further isolated by standard means, such as chromatography or distillation.

In the described processes, solid silicon monoxide is made to react with the organic halide as if the silicon monoxide were an equimolar mixture of reactive silicon and inert silicon dioxide. Therefore, the reactive portion of silicon monoxide represents about 31.85 weight percent of the solid. The spent bed resulting from the described processes can be reactivated by the instant described heat activating process and further conversion of silicon achieved. In addition, unreacted silicon, as silicon dioxide, can be recovered and, for example, recycled as feed to a process for making silicon metal or silicon monoxide. The unreacted silicon dioxide may also be used as a filler or filler and reinforcing agent. The unreactive silicon dioxide may be used as a filler, for example, in silicone emulsions or as a filler and reinforcing agent in silicone elastomers.

Product silanes which can be produced by the instant described processes can be, for example, silane ($SiH_4$) and non-alkylated halosilanes, for example, mono-, di-, tri- and tetra-halosilanes; where the halogen is chloride, bromide, iodide, or fluoride atoms. The halosilanes can be, for example, tetrachlorosilane, trichlorosilane, dichlorosilane, chlorosilane, tetrabromosilane, tribromosilane, tetrafluorosilane, and trifluorosilane.

The silanes which can be formed by the described processes include alkyl substituted silanes. The alkyl silane can be the mono-, di-, tri-, and tetra- alkylsilanes; where the alkyl group, R, is a hydrocarbon of one to six carbon atoms. R can be, for example, methyl, ethyl, propyl, butyl, pentyl, hexyl, isopropyl, isobutyl, tert-butyl, or isopentyl radicals. The alkylsilane can be, for example, tetramethylsilane, trimethylsilane, dimethylsilane, methylsilane, tetraethylsilane, triethylsilane, diethylsilane, and ethylsilane.

The silanes which can be formed by the described process include alkyl halosilanes, for example, methyldichlorosilane, methyltrichlorosilane, dimethylchlorosilane, dimethyldichlorosilane, trimethylchlorosilane, methyltriiodosilane, methyldiiodosilane, dimethyldiiodosilane, methyltribromosilane, methyldibromosilane, dimethyldibromosilane, methyltrifluorosilane, methyldifluorosilane, methylfluorosilane, dimethyldifluorosilane, ethyldichlorosilane, ethyltrichlorosilane, diethyldichlorosilane, and triethylchlorosilane.

The silanes which can be formed by the described processes include alkenylsilanes. The alkenyl silane can be the mono-, di-, tri-, and tetra- alkenylsilane, where the alkenyl group, R, is a hydrocarbon of one to six carbon atoms. R can be, for example, vinyl, allyl, hexenyl, and butenyl radicals.

The alkenylsilane can be, for example, tetravinylsilane, trivinylsilane, divinylsilane, vinylsilane, tetraallylsilane, triallylsilane, triallylsilane, diallylsilane, and allylsilane.

The silanes which can be formed by the described process include alkenylhalosilanes, for example, vinyldichlorosilane, vinyltrichlorosilane, divinyldichlorosilane, trivinylchlorosilane, allyldichlorosilane, allyltrichlorosilane, diallyldichlorosilane, and triallyldichlorosilane.

The silanes which can be formed by the described process may include alkenylalkylsilanes and alkenylalkylhalosilanes, for example, vinylmethylsilane, vinylmethyldichlorosilane, vinyltrimethylsilane, and trivinylmethylsilane.

So that those skilled in the art may better understand the instant described processes, the following examples are offered as illustrative of the instant invention. The examples are not intended to be limiting on the processes as described herein.

EXAMPLE 1

(Not Within the Scope of the Present Invention.)

The reactivity of methylchloride with silicon monoxide was evaluated in a fixed-bed reactor.

The fixed-bed reactor consisted of a vertical one-inch diameter quartz tube. The quartz tube contained on the lower end a quartz-wool plug for supporting a particulate bed. The reactor was heated in a tube furnace. Feed gases entered at the top of the reactor and flowed downward through the fixed bed. Product silanes were collected in a dry ice cooled cold trap located at the reactor's exit. The mixture collected in the cold trap was analyzed by gas chromatography.

Particulate silicon monoxide, with a nominal purity of greater than 99.95 percent, was purchased from Alfa Products (Danvers, MA). The particle size of the silicon monoxide was less than 120 mesh. A total of 1.6 grams of silicon monoxide was added to the reactor. A mixture of 11 percent methylchloride in helium was passed through the fixed-bed at a rate of 75 standard cubic centimeters per minute (sccm) for a period of 21 hours. The temperature of the reactor was increased stepwise from 400° C. to 800° C. during a 21 hour reaction time period. No conversion of silicon monoxide to silanes was detected.

EXAMPLE 2

Cuprous chloride (CuCl), was evaluated as a catalyst for the reaction of silicon monoxide with methylchloride to form silanes.

A fixed-bed reactor similar to that described in Example 1 was employed. Cuprous chloride (Calabrian Chemical, Houston, TX) was mixed with silicon monoxide at 4.25 percent of the combined total weight of CuCl and silicon monoxide. The silicon monoxide was of 99.95% purity with a nominal particle size of two microns (Alfa Products, Danvers, MA). A total weight of 3.5 grams of the mixture was placed in the reactor to form a reaction bed. The reactor was purged with helium for about 30 minutes. The silicon monoxide, mixed with the catalyst, was activated by passing helium through the reaction bed at a rate of 30 sccm at a reactor temperature of 165° C., for a period of 12 hours. After activation of the silicon monoxide, methylchloride gas was passed through the reaction bed at a rate of 10 sccm. The reaction was run for eight hours at 350° C. The results are presented in Table 1. The percent conversion of the available silicon (% Conv) to silanes was calculated. By the described process, solid silicon monoxide is made to react as if it were an equimolar mixture of reactive silicon and inert silicon dioxide. Therefore, the reactive portion of SiO represents 31.85 weight percent of the solid. For this reason, conversions of the solid silicon monoxide are expressed as the percentage of available silicon converted to silane products. The percent conversion values were calculated as:

$$\%\text{Conv.} = 100 \times (\text{Si in products (g)}/(0.3185 \times \text{SiO added to reactor (g)}).$$

Selectivity of the reaction, for product, was calculated directly from the amounts of each silane product formed in proportion to the percent total product formed, as determined by chromatographic analysis. That is:

$$\text{Selectivity (wt \%)} = 100 \times (\text{specific product formed (g)}/\text{total silane product (g)}).$$

TABLE 1

Cuprous Chloride as Catalyst For The Reaction of Activated Silicon Monoxide With Methylchloride

| Run | Reaction (h) | (°C.) | % Conv | Selectivity (wt %) | | | | | |
|---|---|---|---|---|---|---|---|---|---|
| | | | | MeHSiCl$_2$ | Me$_3$SiCl | MeSiCl$_3$ | Me$_2$SiCl$_2$ | HSiCl$_3$ | SiCl$_4$ |
| 39 | 8 | 350 | 0.7 | trace | — | 11.4 | — | 1.7 | 87.0 |

The data presented in Table 1 demonstrate the ability of CuCl to facilitate the reaction of silicon monoxide with methylchloride.

EXAMPLE 3

A series of runs were made to evaluate the effect of activation temperature on silicon monoxide conversion and product selectivity.

The reactor was a fixed-bed type, as previously described. The silicon monoxide, purchased from Cerac (Milwaukee, WI), had a nominal purity of 99.99% and a nominal particle size less than 325 mesh. A catalyst mixture resulting in a final concentration in the silicon monoxide of 6.23 wt % CuCl powder, 60 ppm tin, 600 ppm brass, 1500 ppm aluminum, and 2000 ppm of a copper and phosphorous alloy (Cu+P), all values expressed in relation to total combined weight of catalyst and silicon monoxide, was employed.

Eight to ten grams of silicon monoxide and catalyst mixture were added to the reactor to form a fixed-bed. The reactor was purged with helium. The fixed-bed was then activated under a helium flow of eight sccm, for one hour, at temperatures given in Table 2. Run number 23 was run under a helium flow of 50 sccm. After completion of the activation process, methylchloride gas was passed through the fixed-bed at a rate of 24 sccm, at a reactor temperature of 330° C. Product silanes were collected and analyzed as previously described. The results of these runs are presented in Table 2. The activation time (h) and temperature (°C.) are presented in Table 2. Other headings of Table 2 are as previously described.

contained an expanded orifice to allow addition of solids and two ground-glass joints serving as inlet and exit ports. The system was equipped with electronic mass flow controllers to feed gases to the reactor. Gases entered through the inlet port, which was connected to a narrow tube which ended near the bottom of the reactor. Gases flowed upward through the reactor bed and exited through the exit port near the top of the reactor. The bottom section of the reactor was immersed in a fluidized sand bath of provide heat to the reactor. The reactor and fluidized sand bath were mounted on a vibrating platform. Silane products and unreacted methylchloride exiting the reactor were condensed and collected in a cold trap cooled to minus 80° C.

Silicon monoxide, purchased from Alfa Products (Danvers, MA), with a purity greater than 99.95 percent and a nominal particle size of two micron was employed. A catalyst mixture was prepared consisting of, by weight: 1 part tin, 10 parts brass, 24 parts aluminum, 32 parts copper and phosphorous alloy, and 1000 parts CuCl. The concentration of catalyst mixture in the reactor charge was varied as indicated in Table 3.

Twenty grams of the silicon monoxide and catalyst mixture was placed in the vibrating-bed reactor. The reactor was purged with nitrogen for about 30 minutes. The silicon monoxide and catalyst mixture was activated by bringing the reactor temperature to 330° C. and passing nitrogen gas through the reactor at a rate of 60 sccm for one hour. After the activation procedure, the silicon monoxide was reacted with methylchloride metered to the reactor at a rate of 30 sccm for 43 hours.

TABLE 2

Effect of Activation Temperature on Silicon Monoxide Reaction With Methylchloride in The Presence of Catalyst

| Run | Activation (h) | (°C.) | % Conv | Selectivity (wt %) | | | | | |
|---|---|---|---|---|---|---|---|---|---|
| | | | | MeHSiCl$_2$ | Me$_3$SiCl | MeSiCl$_3$ | Me$_2$SiCl$_2$ | HSiCl$_3$ | SiCl$_4$ |
| 12 | 1 | 200 | 4.3 | 22.2 | 0.9 | 43.9 | 6.4 | 9.9 | 16.7 |
| 17 | 1 | 425 | 1.2 | 25.1 | — | 61.7 | 7.5 | 0.7 | 5.0 |
| 23 | 1 | 550 | 0.5 | — | — | 44.7 | 26.1 | — | 29.2 |
| 10 | 1 | 800 | 1.2 | — | 1.0 | 41.6 | 50.0 | — | 7.4 |
| 16 | 1 | 1050 | 4.5* | 4.2 | 2.8 | 24.4 | 64.9 | — | 1.3 |

*Includes 2.4 wt % Me$_2$HSiCl

From the data in Table 2, it can be seen that conversion is greatest at the low and high end of the activation temperature range evaluated. Conversion passes through a minimum at an activation temperature of 550° C. Selectivity to Me$_2$SiCl$_2$ increases dramatically at higher activation temperatures.

EXAMPLE 4

The effect of varying the level of a standard catalyst mixture on the reaction of silicon monoxide with methylchloride was evaluated. For this series of runs, a vibrating-bed reactor was employed. The vibrating-bed reactor consisted of a 19 mm diameter Pyrex-glass tube closed at the bottom end. The top section of the tube During the reaction period, the temperature of the reactor was maintained at 330° C. The results are present in Table 3. The headings of Table 3 are the same as previously described. The additional heading "Catalyst(wt %)" is calculated as the weight of the catalyst mixture divided by the weight of the catalyst mixture and silicon monoxide combined, the value being multiplied by 100.

TABLE 3

Effect of Catalyst Levels on Reaction of Activated Silicon Monoxide With Methylchloride

| Run | Catalyst (wt %) | % Conv | Selectivity (wt %) | | | | | |
|---|---|---|---|---|---|---|---|---|
| | | | MeHSiCl$_2$ | Me$_3$SiCl | MeSiCl$_3$ | Me$_2$SiCl$_2$ | HSiCl$_3$ | SiCl$_4$ |
| 51-1 | 3.36 | 0.6 | 1.9 | 5.1 | 70.1 | 7.4 | — | 15.6 |
| 51-2 | 6.91 | 4.2 | 18.4 | 2.0 | 60.2 | 8.3 | 3.2 | 7.9 |
| 51-3 | 13.18 | 9.4 | 6.3 | 0.7 | 64.6 | 4.4 | 9.4 | 14.7 |
| 51-4 | 20.08 | 16.0 | — | 0.1 | 38.1 | 0.5 | 35.3 | 25.8 |

The data in Table 3 illustrate that the conversion of silicon monoxide to silanes increases with increasing catalyst concentration. The selectivity for Me$_2$SiCl$_2$ appears to reach a peak between 3.36 wt % and 13.18 wt % catalyst.

EXAMPLE 5

A number of materials were tested in combination with CuCl as catalysts for the reaction of silicon monoxide with methylchloride. A vibrating-bed reactor, as previously described, was employed. The silicon monoxide which was employed was purchased from Cerac Inc. (Milwaukee, Wi.), and had a purity of 99.99% and a nominal particle size of less than 325 mesh. Materials tested as catalysts were CuCl (Cuprous Chloride, Type II, Calabrian Chemical, Houston, Tx.), Aluminum metal (Grade 44, 20-34 micron aluminum powder, Alcan Aluminum, Joliet, Il.), $SnCl_2$ (Anhydrous 98% Tin (II) Chloride, Alfa Products, Danvers, Ma.), $ZnCl_2$ (Granular Zinc Chloride, Mallinckrodt Chemical, Paris, Ky.), and $AlCl_3$ (anhydrous aluminum chloride powder, Mallinckrodt Chemical, Paris, Ky.).

The silicon monoxide was mixed with the materials to be tested as catalysts by placing all in a container and shaking for approximately 30 minutes. Fifteen to 20 grams of the silicon monoxide and catalyst mixture was placed in the reactor and the reactor purged with helium for about 30 minutes. After purging of the reactor, the mixture was activated by heating one hour at 330° C. under a flow of helium at 30 sccm.

Methylchloride, at a flow rate of 30 sccm, was then fed to the reactor for 24 hours. During the reaction, the temperature of the reactor was maintained at 330° C. The results are presented in Table 4. The amounts of aluminum present in the catalyst, Al (ppm), is expressed as parts per million of the combined catalyst and silicon monoxide weight. Other materials tested as catalysts are listed under the heading "Other" and the concentration, as a weight percent (wt %) of the combined catalyst and silicon monoxide weight, is presented. Other headings of Table 4 are as previously described.

TABLE 4
Effect of Metal and Metal Salts on CuCl As a Catalyst for the Reaction of Activated Silicon Monoxide With Methylchloride

| | Catalyst | | | | Selectivity (wt %) | | | |
| --- | --- | --- | --- | --- | --- | --- | --- | --- |
| Run | CuCl (wt %) | Al (ppm) | Other (wt %) | % Conv | MeHSiCl$_2$ | Me$_3$SiCl | MeSiCl$_3$ | Me$_2$SiCl$_2$ |
| 3-2 | 4.01 | — | — | 0.02 | — | — | — | — |
| 8-4 | 4.03 | 2030 | — | 3.03 | 17.3 | 3.2 | 46.7 | 5.9 |
| 9-1 | 4.03 | 2100 | 0.3 SnCl$_2$ | 2.52 | 10.4 | 2.3 | 64.3 | 7.9 |
| 9-3 | 4.02 | 2430 | 5.1 SnCl$_2$ | 7.10 | — | 2.9 | 36.8 | 2.7 |
| 8-1 | 4.01 | 2100 | 0.2 ZnCl$_2$ | 3.91 | 18.1 | 2.9 | 60.6 | 7.3 |
| 8-2 | 4.02 | 2190 | 1.0 ZnCl$_2$ | 9.56 | 26.2 | 1.3 | 57.5 | 6.1 |
| 8-3 | 4.00 | 2080 | 5.3 ZnCl$_2$ | 22.56 | 26.0 | — | 45.1 | 1.6 |
| 6-3 | 4.00 | 2280 | 1.0 AlCl$_3$ | 9.22 | 22.3 | 1.3 | 41.0 | 5.8 |

The data presented in Table 4 demonstrate that silicon monoxide conversion and selection of silane products can be impacted by a variety of compounds. The data indicate tin compounds, zinc compounds, and aluminum compounds can act as effective catalysts. Aluminum and aluminum compounds are particularly effective in increasing silicon monoxide conversion to Me$_2$SiCl$_2$.

EXAMPLE 6

The reactivity of ethylchloride with activated silicon monoxide, in the presence of a catalyst mixture, was evaluated.

The reactor was a fixed-bed type as previously described for Example 2. The silicon monoxide, purchased from Cerac (Milwaukee, WI), had a nominal purity of 99.99% and a nominal particle size less than 325 mesh. The catalyst mixture employed is described in Table 5. The concentration of catalyst ingredients (Conc. Cat.) are given as weight percent (wt %) or parts per million (ppm) of total charge to the reactor. The source of catalyst ingredients were as previously described. Ten grams of silicon monoxide and catalyst mixture were added to the reactor to form a fixed-bed charge. The reactor was purged and maintained under a flow of helium at 50 sccm during the activation process. The reactor charges were activated, at temperatures specified in Table 6, for 1 hour. Ethylchloride was fed to the reactor at a rate of 18 sccm during the reaction process. The reaction was run for a period of 18 hours at a reactor temperature of 310° C. The headings for Table 5 are as previously described.

TABLE 5
Reactivity of Ethylchloride With Activated Silicon Monoxide In The Presence of a Catalyst

| Run | Cat. | Conc. Cat. | Act. (°C.) | % Conv | Selectivity (wt %) | | | |
| --- | --- | --- | --- | --- | --- | --- | --- | --- |
| | | | | | EtHSiCl$_2$ | Et$_2$SiCl$_2$ | EtSiCl$_3$ | SiCl$_4$ |
| 40 | CuCl | 6.3 (wt %) | 1050 | 3.61 | 20.5 | 24.2 | 45.2 | 10.1 |
| | ZnCl$_2$ | 2.2 (wt %) | | | | | | |
| | Sn | 60 (ppm) | | | | | | |
| | Brass | 570 (ppm) | | | | | | |
| | Al | 1430 (ppm) | | | | | | |
| | Cu + P | 1900 (ppm) | | | | | | |
| 41 | CuCl | 8.0 (wt %) | 1050 | 3.59 | 16.0 | 29.4 | 48.0 | 6.6 |
| | ZnCl$_2$ | 0.0 (wt %) | | | | | | |
| | Sn | 120 (ppm) | | | | | | |
| | Brass | 1200 (ppm) | | | | | | |
| | Al | 2980 (ppm) | | | | | | |
| | Cu + P | 3980 (ppm) | | | | | | |
| 42 | CuCl | 6.2 (wt %) | 310 | 0.02 | 0.0 | 0.0 | 100 | 0.0 |
| | ZnCl$_2$ | 1.8 (wt %) | | | | | | |
| | Sn | 60 (ppm) | | | | | | |
| | Brass | 640 (ppm) | | | | | | |

TABLE 5-continued

Reactivity of Ethylchloride With Activated Silicon Monoxide In The Presence of a Catalyst

| Run | Cat. | Conc. Cat. | Act. (°C.) | % Conv | Selectivity (wt %) | | | |
|---|---|---|---|---|---|---|---|---|
| | | | | | EtHSiCl$_2$ | Et$_2$SiCl$_2$ | EtSiCl$_3$ | SiCl$_4$ |
| | Al | 1590 (ppm) | | | | | | |
| | Cu + P | 2120 (ppm) | | | | | | |

The data of Table 5 demonstrate the importance of activation temperature in determining selectivity of the process for particular species of silanes and the effect of activation on overall conversion rate of silicon monoxide.

What is claimed is:

1. A process for preparing silanes, the process comprising:
   (A) contacting silicon monoxide, an organic halide of formula

RX, where X is a halogen and R is selected from a group consisting of alkyl and alkenyl radicals of one to six carbon atoms, and a catalyst effective in facilitating reaction of the solid silicon monoxide with the organic halide; at a reaction temperature of 200° C. to 1200° C.; and
   (B) forming silanes of formula $H_aR_bSiX_{4-a-b}$, where a is an integer from 0 to 4, b is an integer from 0 to 4, a+b is an integer from 0 to 4, and R and X are as previously described.

2. A process according to claim 1, where the organic halide is selected from a group consisting of methylchloride, ethylchloride, and vinylchloride.

3. A process according to claim 1, where the organic halide is methylchloride.

4. A process according to claim 1, where the reaction temperature is 300° C. to 900° C.

5. A process according to claim 1, where the catalyst is selected from the group consisting of copper and copper compounds, tin and tin compounds, zinc and zinc compounds, antimony and antimony compounds, manganese and manganese compounds, mercury and mercury compounds, iron and inorganic iron compounds, nickel and nickel compounds, phosphorous, metal phosphides, metal phosphorous alloys, aluminum and aluminum compounds, and mixtures thereof.

6. A process according to claim 1, where the catalyst is a combination of cuprous chloride, tin, brass, aluminum, and a copper and phosphorous alloy.

7. A process according to claim 1, where the catalyst is cuprous chloride.

8. A process according to claim 7, where the organic halide is methylchloride.

9. A process according to claim 1, further comprising heat activating the silicon monoxide at an activation temperature of 50° C. to 1200° C., for an activation time of 0.5 to 20 hours, prior to contact with the organic halide.

10. A process according to claim 9, where the catalyst is contacted with the solid silicon monoxide during the heat activation of the solid silicon monoxide.

11. A process according to claim 10, where the organic halide is selected from a group consisting of methylchloride, ethylchloride, and vinylchloride.

12. A process according to claim 11, where the organic halide is methylchloride.

13. A process according to claim 10, where the catalyst is a combination of cuprous chloride, tin, brass, aluminum, and a copper and phosphorous alloy.

14. A process according to claim 10, where the catalyst is cuprous chloride.

15. A process according to claim 10, where the catalyst is a combination of cuprous chloride, aluminum, and a compound selected from a group consisting of SnCl$_2$ ZnCl$_2$, and AlCl$_3$.

16. A process according to claim 10, where the catalyst is a combination of cuprous chloride and aluminum.

17. A process according to claim 10, where the activation temperature is 200° C. to 1050° C.

18. A process according to claim 17, where the activation time is 1 to 20 hours.

19. A process according to claim 10, where the reaction temperature is about 300° C. to about 900° C.

20. A process according to claim 10, where the catalyst is a mixture of cuprous chloride, tin, brass, aluminum, and a copper and phosphorous alloy; the organic halide is methylchloride; the activation temperature is about 200° C. to about 1050° C.; the activation time is 1 to 20 hours; and the reaction temperature is about 300° C. to 900° C.

21. A process according to claim 10, where the catalyst is present as a mixture comprising 3.0 to 20.0 weight percent cuprous chloride, 10 to 200 ppm tin, 300 to 1900 ppm brass, 760 to 4600 ppm aluminum, and 1000 to 6100 ppm of a copper and phosphorus alloy, all concentrations expressed in relation to the combined weight of the catalyst and the silicon monoxide.

22. A process according to claim 21, where the activation temperature is 200° C. to 1050° C.; the activation time is 1 to 20 hours; the organic halide is methylchloride; and the reaction temperature is 300° C. to 900° C.

23. A process according to claim 21, where the activating temperature is 200° C. to 1050° C.; the activation time is 1 to 20 hours; the organic halide is ethylchloride; and the reaction temperature is 300° C. to 900° C.

24. A process according to claim 10, where unreacted silicon monoxide and catalyst is re-activated by heating at an activation temperature of 50° C. to 1200° C., for an activation time of 0.5 to 20 hours, prior to contact with the organic halide.

25. A process according to claim 1, where the silanes comprise dimethyldichlorosilane.

26. A process according to claim 1, where the silanes comprise trimethylchlorosilane.

27. A process according to claim 1, where the silanes comprise methyldichlorosilane.

* * * * *